(12) United States Patent
Brandt et al.

(10) Patent No.: US 9,981,117 B2
(45) Date of Patent: May 29, 2018

(54) IMPLANTABLE INFUSION DEVICES AND ASSOCIATED METHODS

(71) Applicant: Medallion Therapuetics, Inc., Santa Clarita, CA (US)

(72) Inventors: William A. Brandt, Castaic, CA (US); Daniel Hernandez Villegas, Porter Ranch, CA (US)

(73) Assignee: Medallion Therapeutics, Inc., Santa Clarita, CA (US)

( * ) Notice: Subject to any disclaimer, the term of this patent is extended or adjusted under 35 U.S.C. 154(b) by 189 days.

(21) Appl. No.: 14/226,731

(22) Filed: Mar. 26, 2014

(65) Prior Publication Data

US 2014/0207085 A1    Jul. 24, 2014

Related U.S. Application Data

(63) Continuation of application No. 12/763,504, filed on Apr. 20, 2010, now Pat. No. 8,721,605.

(60) Provisional application No. 61/173,124, filed on Apr. 27, 2009.

(51) Int. Cl.
*A61M 39/02* (2006.01)
*A61M 5/142* (2006.01)
*A61M 5/168* (2006.01)

(52) U.S. Cl.
CPC .... *A61M 39/0247* (2013.01); *A61M 5/14276* (2013.01); *A61M 5/16827* (2013.01); *A61M 39/0208* (2013.01); *A61M 2039/0217* (2013.01); *A61M 2039/0226* (2013.01); *A61M 2039/0241* (2013.01); *A61M 2039/0244* (2013.01); *A61M 2205/3523* (2013.01); *A61M 2205/3561* (2013.01)

(58) Field of Classification Search
CPC .......... A61M 5/14276; A61M 39/0208; A61M 2039/0211; A61M 2209/045; A61M 2039/0081; A61M 2039/0217; A61M 2205/3331; A61M 39/04; A61M 5/16827; A61M 2039/0226; A61M 2039/0241; A61M 2039/0244; A61M 2205/3523; A61M 2205/3561; A61M 39/0247; A61M 39/26; A61M 5/141; A61M 5/165
See application file for complete search history.

(56) References Cited

U.S. PATENT DOCUMENTS

| | | | |
|---|---|---|---|
| 3,126,031 A | 3/1964 | Hayner | |
| 4,003,379 A | 1/1977 | Ellinwood | |
| 4,072,146 A | 2/1978 | Howes | |
| 4,193,397 A | 3/1980 | Tucker et al. | |
| 4,265,241 A | 5/1981 | Portner et al. | |
| 4,373,527 A | 2/1983 | Fischell | |
| 4,443,218 A * | 4/1984 | DeCant, Jr. ....... | A61M 5/14276 128/DIG. 12 |
| 4,449,983 A | 5/1984 | Cortese et al. | |
| 4,557,722 A | 12/1985 | Harris | |

(Continued)

FOREIGN PATENT DOCUMENTS

| | | |
|---|---|---|
| EP | 1520595 B1 | 1/2007 |
| WO | WO 2005002642 A2 | 1/2005 |
| WO | WO 2005007223 A2 | 1/2005 |

*Primary Examiner* — Bhisma Mehta
*Assistant Examiner* — Brandy S Lee
(74) *Attorney, Agent, or Firm* — Henricks, Slavin & Holmes LLP

(57) ABSTRACT

Implantable infusion devices configured to improve fill and evacuation procedures.

12 Claims, 10 Drawing Sheets

(56) References Cited

U.S. PATENT DOCUMENTS

| | | |
|---|---|---|
| 4,573,994 A | 3/1986 | Fischell et al. |
| 4,588,394 A | 5/1986 | Schulte et al. |
| 4,634,427 A | 1/1987 | Hannula et al. |
| 4,718,893 A | 1/1988 | Dorman et al. |
| 4,871,351 A | 10/1989 | Feingold |
| 4,894,057 A | 1/1990 | Howes et al. |
| 4,955,861 A * | 9/1990 | Enegren ............ A61M 5/14276 604/141 |
| 5,207,642 A | 5/1993 | Orkin et al. |
| 5,240,713 A | 8/1993 | Ayer |
| 5,607,393 A | 3/1997 | Ensminger et al. |
| 5,718,678 A | 2/1998 | Fleming et al. |
| 5,957,890 A * | 9/1999 | Mann ................ A61M 5/14276 604/131 |
| 6,436,091 B1 | 8/2002 | Harper |
| 6,471,688 B1 | 10/2002 | Harper |
| 6,520,936 B1 | 2/2003 | Mann |
| 6,554,822 B1 * | 4/2003 | Holschneider .... A61M 5/14276 604/156 |
| 6,652,510 B2 | 11/2003 | Lord et al. |
| 6,902,544 B2 | 6/2005 | Ludin et al. |
| 6,962,580 B2 | 11/2005 | Adams et al. |
| 7,083,593 B2 | 8/2006 | Stultz |
| 7,131,967 B2 | 11/2006 | Gray et al. |
| 8,002,747 B2 | 8/2011 | Lord et al. |
| 8,721,605 B2 | 5/2014 | Brandt et al. |
| 2001/0020471 A1 | 9/2001 | Kitten |
| 2002/0156462 A1 | 10/2002 | Stultz |
| 2002/0188327 A1 | 12/2002 | Struble |
| 2004/0143242 A1 | 7/2004 | Ludin et al. |
| 2005/0070875 A1 | 3/2005 | Kulessa |
| 2005/0113745 A1 | 5/2005 | Stultz |
| 2006/0142705 A1 | 6/2006 | Halili |
| 2006/0224129 A1 | 10/2006 | Beasley et al. |
| 2006/0270983 A1 * | 11/2006 | Lord ................ A61M 5/14276 604/131 |
| 2006/0271021 A1 | 11/2006 | Steinbach |
| 2008/0243093 A1 | 10/2008 | Kalpin et al. |
| 2009/0264870 A1 * | 10/2009 | Christenson ...... A61M 5/14276 604/891.1 |

\* cited by examiner

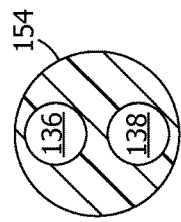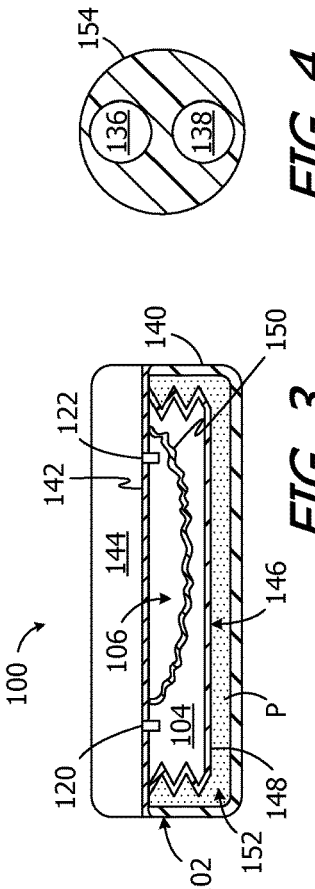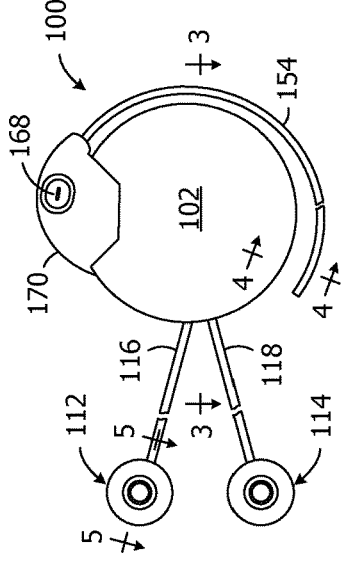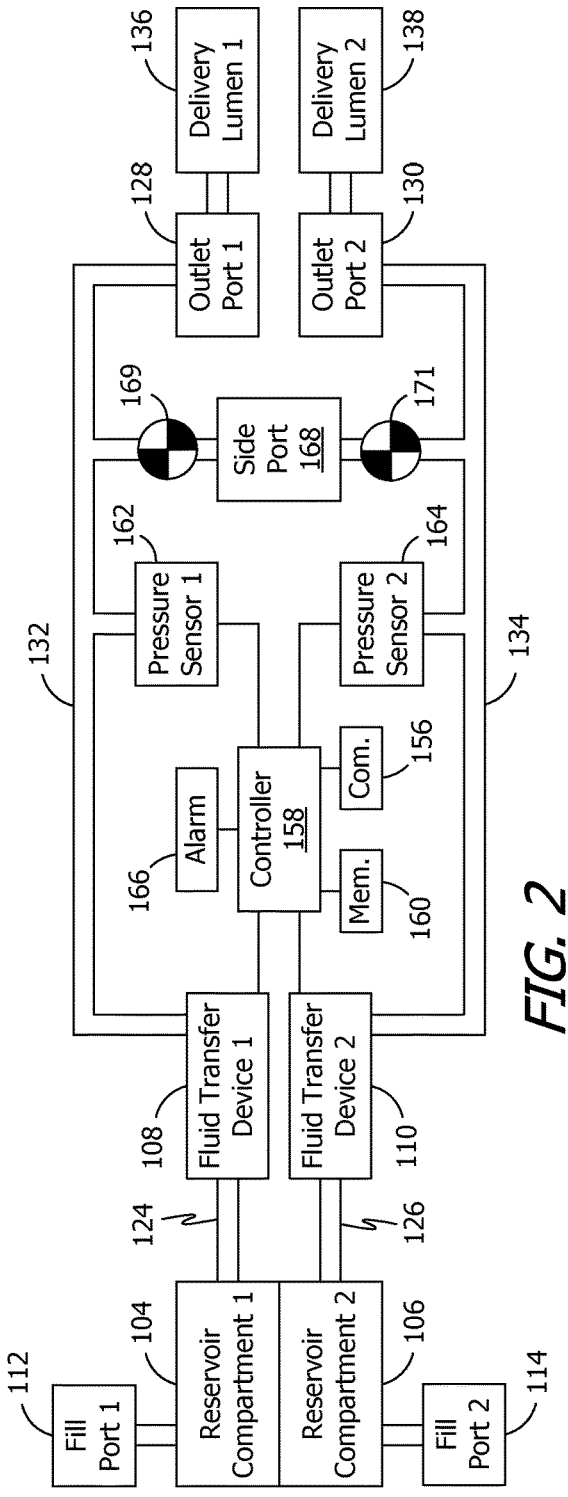

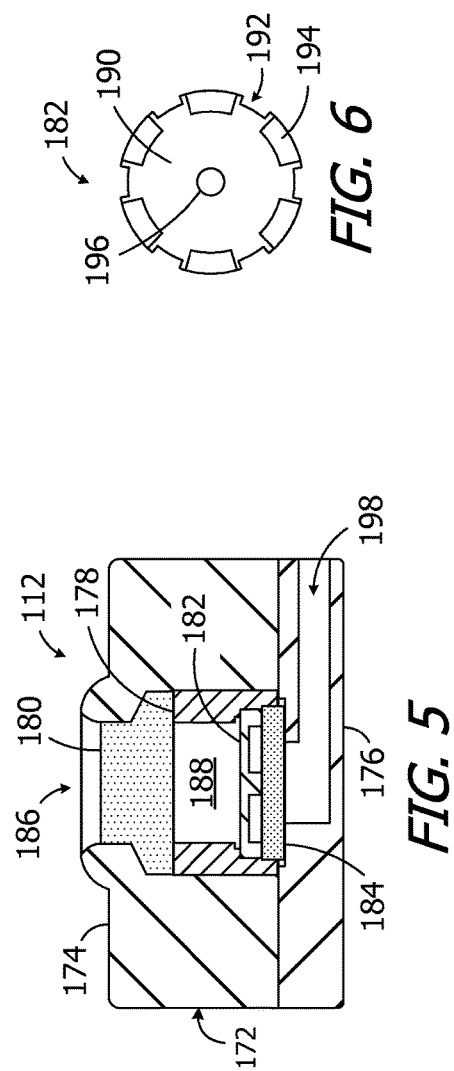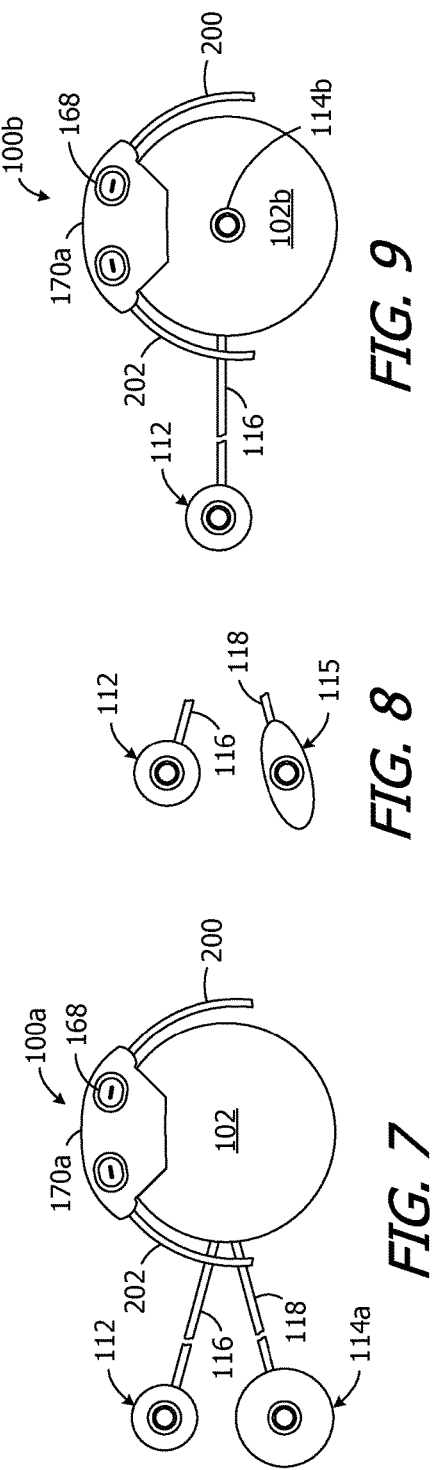

Select Reservoir

Reservoir 1: morphine

Reservoir 2: clonidine

Go Back

*FIG. 14*

Reservoir 2 Inaccessible

Reopen?

Yes    No

*FIG. 16*

Needle in Port?

Yes    No

End

*FIG. 13*

Reservoir 2 Now Accessible

Will Close in 34 Secs.

Close

*FIG. 15*

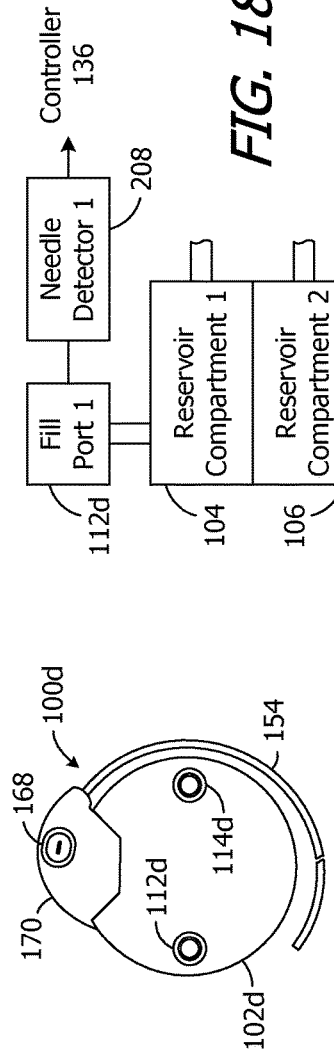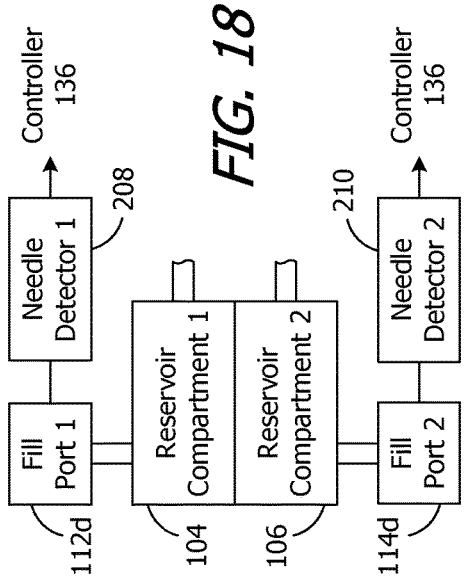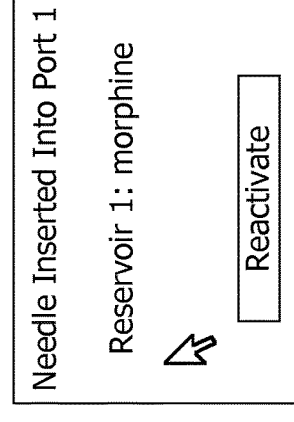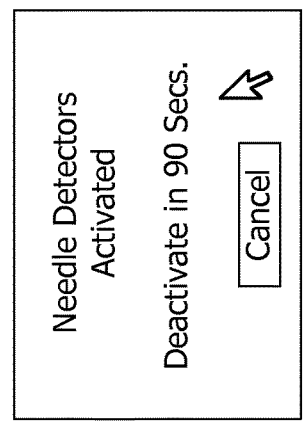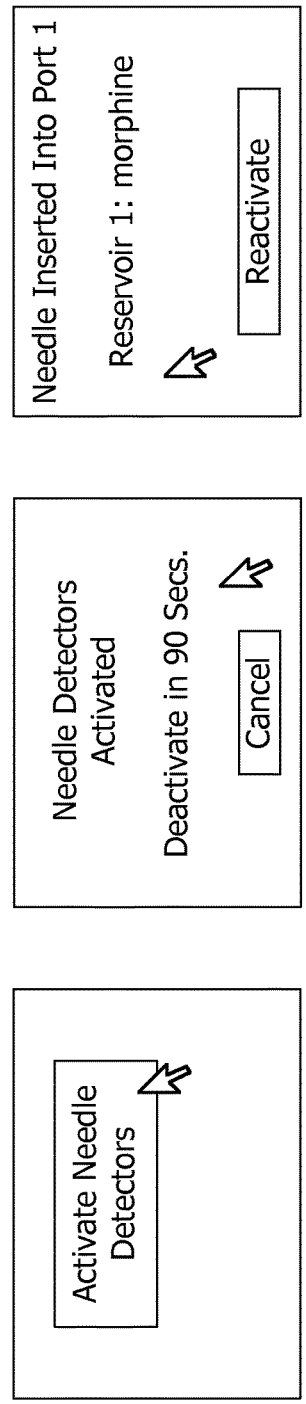

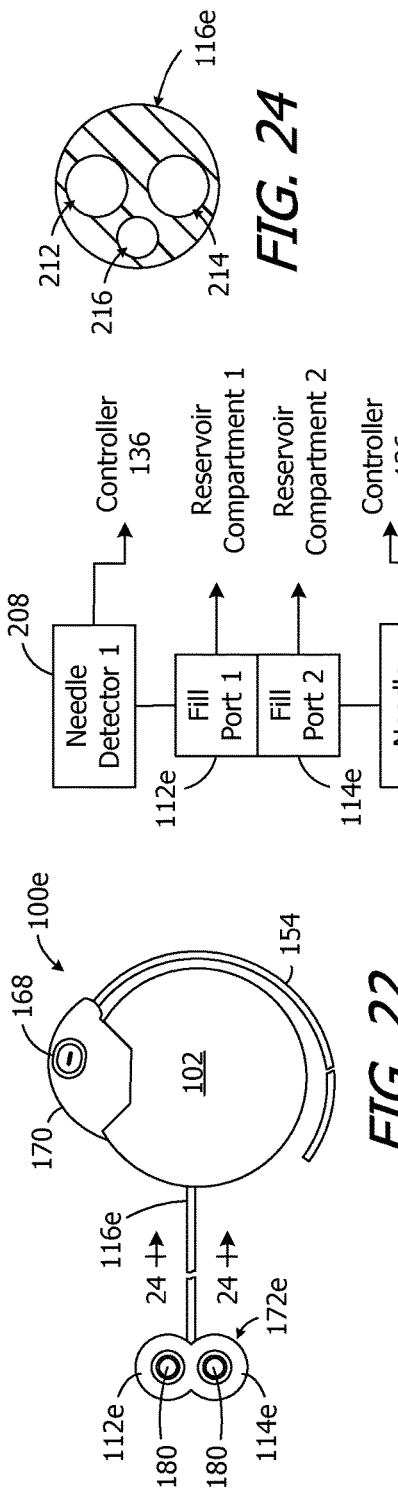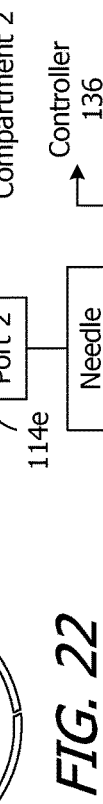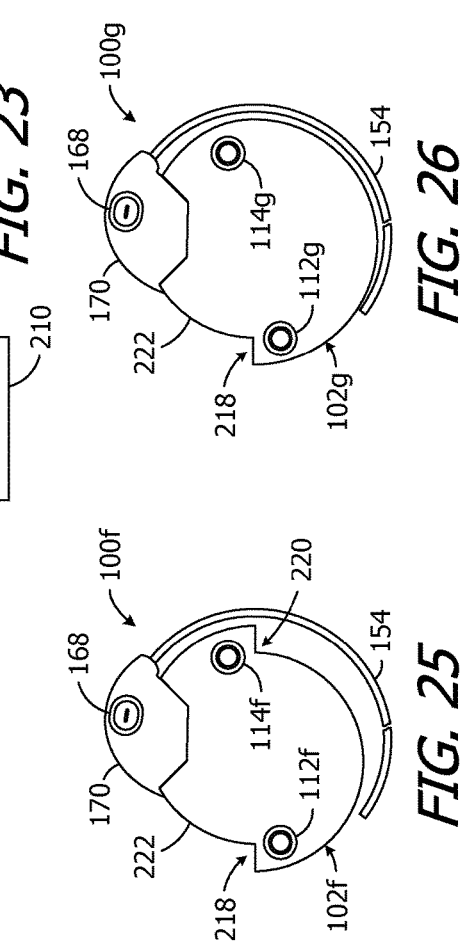

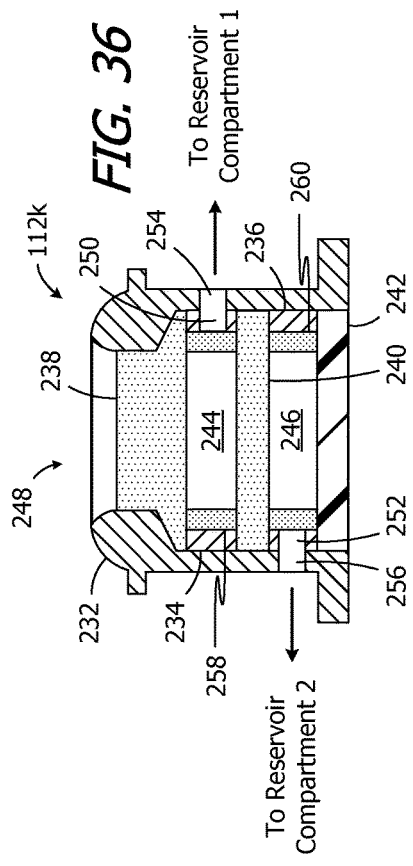
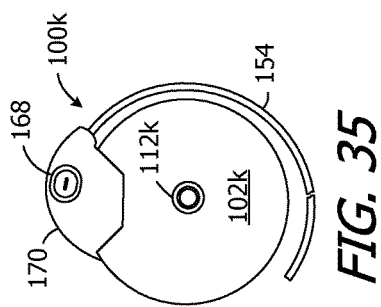
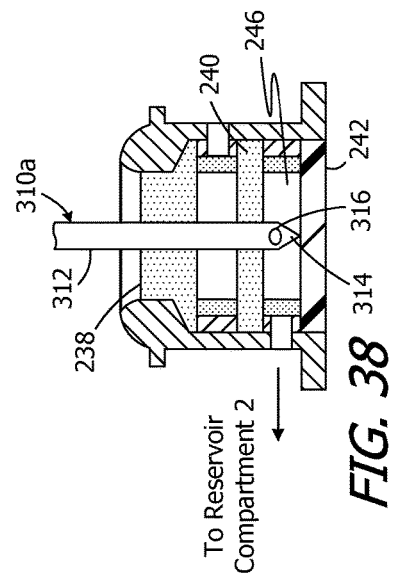
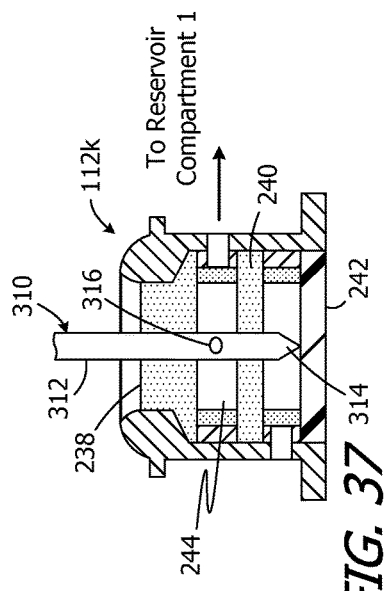

IMPLANTABLE INFUSION DEVICES AND ASSOCIATED METHODS

CROSS-REFERENCE TO RELATED APPLICATIONS

This application is a continuation of U.S. application Ser. No. 12/763,504, filed Apr. 20, 2010, now U.S. Pat. No. 8,721,605, which claims the benefit of U.S. Provisional Application Ser. No. 61/173,124, filed Apr. 27, 2009 and entitled "Implantable Infusion Devices and Associated Methods," which is incorporated herein by reference.

BACKGROUND

1. Field

The present application relates generally to implantable infusion devices.

2. Description of the Related Art

Implantable infusion devices have been used to provide a patient with a medication or other substance (collectively "infusible substance") and frequently include a reservoir and a pump. The reservoir is used to store the infusible substance and, in some instances, a fill port is provided that allows the reservoir to be transcutaneously filled (and/or re-filled) with a hypodermic needle. The reservoir is coupled to the pump, which is in turn connected to an outlet port. A catheter or other device, which has at least one outlet at the target body region, may be connected to the outlet port. As such, infusible substance may be transferred from the reservoir to the target body region by way of the pump and catheter.

In some therapies, there is a need to deliver two or more distinct medications to different body sites or to the same site independently. With some pain management protocols, for example, it is desirable to deliver morphine and clonidine to a patient's intrathecal site. In certain cancer therapies, it may be desirable to deliver multiple medications to multiple sites. As a further example, insulin and glucogon may be administered sequentially to lower or to raise blood sugar in some diabetes therapies. Implantable infusion devices having two or more reservoirs, or two or more reservoir compartments, and two or more fill ports have been proposed in order to accommodate such therapies (collectively "multiple-reservoir implantable infusion devices").

The present inventors have determined that one issue associated with multiple-reservoir implantable infusion devices is related to transcutaneous filling. In particular, the present inventors have determined that it can be difficult to distinguish between two or more fill ports during a fill or evacuation procedure. Regardless of the number of reservoirs and fill ports, another issue associated with conventional implantable infusion devices is post-implantation rotation of the device. Post-implantation rotation can make it difficult to locate a single fill port, if the fill port is not located in the center of the reservoir, to distinguish between multiple fill ports. Post-implantation rotation can also put strain on catheter, can pull the end of the catheter from its proper position (e.g. within spine), can cause catheter fatigue at the connection to the pump, which leads to breaks and leaks, can cause disconnections at the pump or at the spinal connection of a two-part catheter, and can cause tissue irritation or erosion in the pump pocket.

SUMMARY

An implantable infusion device in accordance with at least one of the present inventions includes an infusion device housing, a first fill port located in spaced relation to the infusion device housing, and a second fill port located in spaced relation to the infusion device housing and the first fill port.

An implantable infusion device in accordance with at least one of the present inventions includes an infusion device housing, a first fill port located in spaced relation to the infusion device housing, and a second fill port carried by the infusion device housing.

An implantable infusion device in accordance with at least one of the present inventions includes first and second reservoir compartments, a single fill port operably connected to the first reservoir compartment by a first flow path and to the second reservoir compartment by a second flow path, and first and second valves respectively associated with the first and second flow paths.

A method in accordance with at least one of the present inventions includes the steps of presenting a choice between the first and second reservoir compartments of an implanted medical device and causing the controller to open a fill port valve associated with the selected one of the first and second reservoir compartments in response to a selection of one of the reservoir compartments.

An implantable infusion device in accordance with at least one of the present inventions includes first and second fill ports and first and second needle detectors respectively associated with the first and second fill ports.

A method in accordance with at least one of the present inventions includes the steps of instructing an implanted infusion device to actuate first and second needle detectors that are associated with first and second fill ports and providing an indication as to which fill port a needle is located in.

An implantable infusion device in accordance with at least one of the present inventions includes an infusion device housing and first and second fill ports associated with the infusion device housing. The infusion device housing includes a first palpable landmark adjacent to the first fill port.

An implantable infusion device in accordance with at least one of the present inventions includes an infusion device housing with a concave rear wall and a convex front wall.

An implantable infusion device in accordance with at least one of the present inventions includes an infusion device housing and first and second fill ports associated with the infusion device housing. The first fill port protrudes outwardly relative to the housing outer surface, and the second fill port is recessed relative to the housing outer surface.

An implantable infusion device in accordance with at least one of the present inventions includes an infusion device housing and first and second fill ports that define different needle access angles.

An implantable infusion device in accordance with at least one of the present inventions includes a fill port with first and second fluid receiving regions that are isolated from one another such that fluid flow therebetween is prevented. The first fluid receiving region may be operably connected to a first reservoir compartment and the second fluid receiving region may be operably connected to a second reservoir compartment. A system in accordance with at least one of the present inventions includes such an implantable infusion device, a first needle that is configured to deliver fluid to the first fluid receiving region, and a second needle that is configured to deliver fluid to the second fluid receiving region.

There are a variety of advantages associated with such devices and methods. By way of example, but not limitation, the present devices and methods reduce the difficulty associated with filling and evacuating conventional implantable infusion devices.

The above described and many other features of the present devices and methods will become apparent as the devices and methods become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

FIG. 1 is a plan view of an implantable infusion device in accordance with one embodiment of a present invention.

FIG. 2 is a block diagram of the exemplary implantable infusion device illustrated in FIG. 1.

FIG. 3 is a partial section view taken along line 3-3 in FIG. 1.

FIG. 4 is a section view of a catheter taken along line 4-4 in FIG. 1.

FIG. 5 is a section view taken along line 5-5 in FIG. 1.

FIG. 6 is a bottom plan view of a needle stop in accordance with one embodiment of a present invention.

FIG. 7 is a plan view of an implantable infusion device in accordance with one embodiment of a present invention.

FIG. 8 is a plan view of implantable infusion device ports in accordance with one embodiment of a present invention.

FIG. 9 is a plan view of an implantable infusion device in accordance with one embodiment of a present invention.

FIGS. 13-16 are screen shots in accordance with one embodiment of a present invention.

FIG. 17 is a plan view of an implantable infusion device in accordance with one embodiment of a present invention.

FIG. 18 is a block diagram of a portion of the implantable infusion device illustrated in FIG. 17.

FIGS. 19-21 are screen shots in accordance with one embodiment of a present invention.

FIG. 22 is a plan view of an implantable infusion device in accordance with one embodiment of a present invention.

FIG. 23 is a block diagram of a portion of the implantable infusion device illustrated in FIG. 22.

FIG. 24 is a section view taken along line 24-24 in FIG. 22.

FIG. 25 is a plan view of an implantable infusion device in accordance with one embodiment of a present invention.

FIG. 26 is a plan view of an implantable infusion device in accordance with one embodiment of a present invention.

FIG. 35 is a plan view of an implantable infusion device in accordance with one embodiment of a present invention.

FIG. 36 is a section view of a fill port in accordance with one embodiment of a present invention.

FIGS. 37 and 38 are partial section views of the fill port illustrated in FIG. 36 in combination with needles.

DETAILED DESCRIPTION OF THE EXEMPLARY EMBODIMENTS

Figure 10:
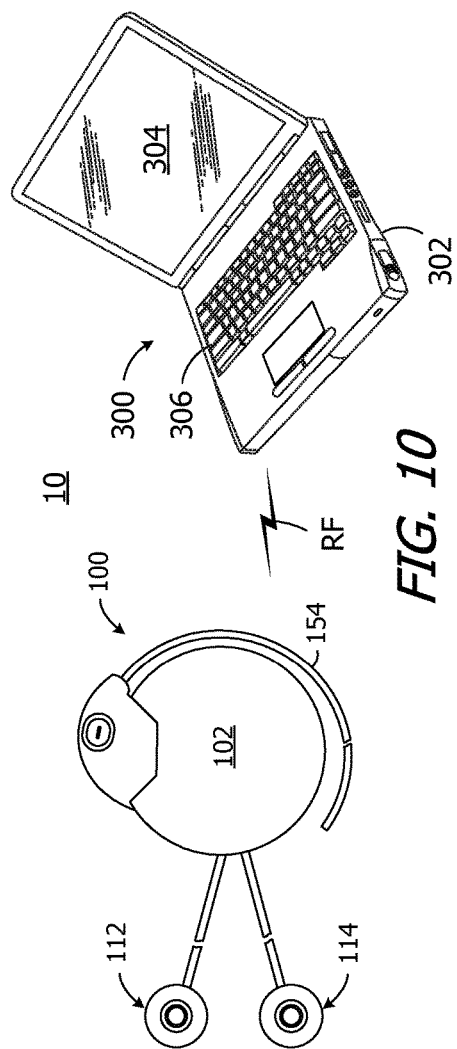
FIG. 10 is a view of an implantable infusion device system in accordance with one embodiment of a present invention.

The following is a detailed description of the best presently known modes of carrying out the inventions. This description is not to be taken in a limiting sense, but is made merely for the purpose of illustrating the general principles of the inventions. The present inventions are also not limited to the exemplary implantable infusion devices described herein and, instead, are applicable to other implantable or otherwise ambulatory infusion devices that currently exist or are yet to be developed.

One example of an implantable infusion device in accordance with at least one of the present inventions is generally represented by reference numeral 100 in FIGS. 1-4. As used herein, an "implantable infusion device" is a device that includes at least one reservoir and at least one outlet, and is sized, shaped and otherwise constructed (e.g. sealed) such that both the reservoir and outlet can be simultaneously carried within the patient's body. The exemplary infusion device 100 includes a housing 102, first and second reservoir compartments 104 and 106, and first and second fluid transfer devices 108 and 110. First and second fill ports 112 and 114, which may be used in fill or evacuation procedures, are respectively connected to the first and second reservoir compartments 104 and 106 by tubes 116 and 118 (e.g. catheter tubes) and internal passages 120 and 122 (FIG. 3). The first and second reservoir compartments 104 and 106 are respectively connected to the fluid transfer devices 108 and 110 by passages 124 and 126 and are connected to first and second outlet ports 128 and 130 by passages 132 and 134. First and second delivery lumens 136 and 138 are respectively connected to the outlet ports 128 and 130. Accordingly, in response to actuation of the fluid transfer devices 108 and 110, fluid will flow to the from the reservoir compartments 104 and 106 to the delivery lumens 136 and 138 and, ultimately, to the patient.

Referring to FIG. 3, the exemplary housing 102 (e.g. a titanium housing) has a bottom portion 140, an internal wall 142, and a cover 144. The reservoir compartments 104 and 106, which each store an infusible substance (e.g. medication), are located within the bottom portion. The electronic components and some of the fluid-related components may be located between the internal wall 142 and the cover 144.

The first and second reservoir compartments 104 and 106, which are volumes within one or more reservoirs, may be formed in a variety of ways. First and second reservoir compartments may, for example, be formed by first and second separate reservoirs. One example of such an arrangement in disclosed in U.S. Pat. No. 7,083,593 to Stultz, which is incorporated herein by reference. In the illustrated embodiment, the first and second reservoir compartments 104 and 106 are formed by a single reservoir 146 with a titanium bellows 148 and a pressure transmissive partition 150 positioned within the reservoir enclosure. One example of such an arrangement in disclosed in greater detail in U.S. Patent Pub. No. 2006/0270983 to Lord, which is incorporated herein by reference. Briefly, the pressure transmissive partition 150 divides the volume within the reservoir 146 into the first and second reservoir compartments 104 and 106. The portion of the sealed volume 152 defined by the housing bottom portion 140 and the internal wall 142 not occupied by the reservoir 146 is occupied by propellant P, which may be used to exert positive or negative pressure on the reservoir. The pressure within the first and second compartments 104 and 106 will be equalized by the pressure transmissive partition 150.

It should also be noted here that, in other implementations, the housing bottom portion and the propellant may be omitted and the single reservoir configured for exposure to the ambient environment. The single reservoir, in some exemplary implementations, may be a negative pressure reservoir that employs a movable wall that is exposed to ambient pressure and is configured to exert a force that produces an interior pressure that is always negative with respect to the ambient pressure. A pressure transmissive partition may be used to divide the volume within the negative pressure reservoir into first and second reservoir compartments. Additional details concerning such reservoirs are provided in U.S. Patent Pub. No. 2006/0270983.

Turning to the first and second fluid transfer devices 108 and 110, a wide variety of fluid transfer devices may be employed. For example, electromagnet piston pumps which have, among other things, an actuator with an electromagnet and an armature, may be employed. One example of such an electromagnet pump is illustrated and described in U.S. Patent Pub. No. 2008/0234639, which is incorporated herein by reference. The present inventions are not, however, limited to electromagnet pumps and may include other types of fluid transfer devices. Such devices include, but are not limited to, other electromagnetic pumps, solenoid pumps, piezo pumps, and any other mechanical or electromechanical pulsatile pump. Additionally, in the context of positive pressure reservoirs, the fluid transfer device may be in the form of an accumulator which includes a variable volume housing and active inlet and outlet valves. First and second fluid transfer devices that share a common actuator, such as those disclosed in U.S. Patent Pub. No. 2006/0270983, may also be employed. Although the volume/stroke magnitude may be increased in certain situations, the fluid transfer devices will typically deliver about 1 microliter/stroke or other actuation, but may be more or less (e.g. about 0.25 microliter/actuation or less) depending on the particular fluid transfer device employed.

In the exemplary implementation illustrated in FIGS. 1-4, the delivery lumens 136 and 138 are located within a single catheter 154. The delivery lumens 136 and 138 may be side-by-side, as shown in FIG. 4, or may be concentric. In other exemplary implementations, the delivery lumens may be located within separate catheters, as is discussed below with reference to FIGS. 7-9. Other embodiments may be configured such that two fluid transfer devices (e.g. fluid transfer devices 108 and 110) pump fluid into a single delivery lumen.

Energy for the fluid transfer devices and other aspects of the exemplary infusion device 100 illustrated in FIGS. 1-4 is provided by the battery (not shown). In some cases, such as where electromagnet piston pumps are employed, the battery may be used to charge one or more capacitors (not shown), and is not directly connected to the fluid transfer device itself. The capacitor(s) are connected to the electromagnet coils, and disconnected from the battery, when the electromagnets are being energized, and are disconnected from the electromagnets and connected to the battery when the capacitor(s) are being recharged and/or when the fluid transfer devices are at rest. A communication device 156, which is connected to an antenna (not shown), may also be provided. Suitable communication devices include, but are not limited to, RF communication devices, oscillating magnetic field communication devices, static magnetic field communication devices, optical communication devices, ultrasound communication devices and direct electrical communication devices.

A controller 158 (FIG. 2), such as a microprocessor, microcontroller or other control circuitry, controls the operations of the infusion device 100 in accordance with instructions stored in memory 160 and/or provided by an external device by way of the communication device 156. For example, the controller 158 carried on a circuit board may be used to control the fluid transfer devices 108 and 110 to supply fluids to the patient in accordance with, for example, a stored delivery profile or a bolus delivery request (generically referred to as a "delivery instruction"). The controller 158 may also be used to monitor a pair of pressure sensors 162 and 164 that are respectively connected to the passageways 132 and 134 between the fluid transfer devices 108 and 110 and the outlet ports 128 and 130. The pressure sensors 162 and 164 sense the pressure at the outlet ports 128 and 130 which, in the illustrated embodiment, is also the pressure within the delivery lumens 136 and 138. An audible alarm 166, which is located within the housing 102 and is connected to the controller 158, may be actuated by the controller if pressure measurements taken by one or both of the pressure sensors 162 and 164 indicates that one or both of the delivery lumens 136 and 138 is blocked.

The exemplary infusion device 100 illustrated in FIGS. 1-4 is also provided with a side port 168 that is connected to the passageways 132 and 134 between the outlets of the fluid transfer devices 108 and 110 and the outlet ports 128 and 130. The side port 168 facilitates access to the delivery lumens 136 and 138, typically by way of a hypodermic needle. For example, the side port 168 allows clinicians to push fluid into the delivery lumens 136 and 138 and/or draw fluid from the delivery lumens for purposes such as checking catheter patency, sampling CSF, injecting contrast dye into the patient and/or catheter, removing medication from the catheter prior to dye injection, injecting additional medication into the region at the delivery lumen outlets, and/or removing pharmaceuticals or other fluids that are causing an allergic or otherwise undesirable biologic reaction. One way valves 169 and 171 (FIG. 2), which prevent fluid within the passageways 132 and 134 from entering the side port 168, may also be provided in order to prevent fluid being pumped through one passageway from entering the other passageway by way of the side port. Although a single side port is connected to both of the outlet ports 128 and 130 in the exemplary embodiment illustrated in FIGS. 1-4, a pair of side ports may be provided in other implementations and each of the side ports is connected to a single outlet port, as is discussed below with reference to FIGS. 7-9.

The outlet ports 128 and 130, portions of the passageways 132 and 134, the communication antenna, and the side port 168 are carried by a header assembly 170. The outlet ports 128 and 130 are adjacent to one another. The header assembly 170 is a molded, plastic structure that is secured to the housing 102. The housing 102 includes a small aperture through which portions of the passageways 132 and 134 extend, and a small aperture through which the antenna is connected to the circuit board.

As noted above, the reservoir compartments 104 and 106 may be replenished by way of the fill ports 112 and 114. A hypodermic needle (not shown), which is configured to be pushed through the fill ports 112 and 114, may be used to selectively replenish the reservoir compartments 104 and 106. Fluid flow from the fill ports 112 and 114 to the reservoir compartments 104 and 106 may be controlled by inlet valves (not shown). As illustrated for example in FIG. 1, the fill ports 112 and 114 are located in spaced relation to the housing 102 and are connected to the remainder of the implantable infusion device 100 in such a manner that they may be located within the patient in spaced relation to one another. In particular, the tubes 116 and 118 are long enough and flexible enough to facilitate the positioning of the fill ports 112 and 114 in spaced relation to one another. The length of the tubes 116 and 118 may be the same or may be different, and suitable lengths range from about 3 inches to about 12 inches, depending on the intended application. One exemplary positioning would be fill port 112 in the patient's abdomen and fill port 114 below the skin above one of the buttocks. The clinician's records would include the location of the fill port associated with the first reservoir compartment 104 as well as the location of the fill port associated with the first reservoir compartment 106.

Although the present inventions are not limited to any particular fill port configuration, the exemplary fill port 112 is illustrated in greater detail in FIGS. 5 and 6 and includes a housing 172 with top and bottom portions 174 and 176, a base 178 and a septum 180. In some instances, such as the illustrated implementation, a needle stop 182 and a filter 184 are also provided. The fill port housing 172 includes a lumen 186 through which a needle may be inserted. The base 178, which supports the septum 180 and centers the needle stop 182 and filter 184, includes an internal lumen 188 into which a needle may be inserted. The septum 180 may, for example, be a self-healing septum formed from materials such as silicone. The needle stop 182 limits needle travel while allowing fluid flow and, in the illustrated embodiment, includes a stop member 190 with a plurality of apertures 192, a plurality of perimeter supports 194, and a center support 196. The supports 194 and 196 create spacing between the stop member 190 and the filter 184 to facilitate fluid flow from the apertures 192 to the entire top surface of the filter. Although other types of filters may be employed, the filter 184 in the illustrated embodiment is a sintered metallic filter. Fluid that passes through the filter 184 exits the fill port 112 and enters the tubes 116 by way of a passage 198. With respect to size, and although the present inventions are not limited to particular sizes, the diameter of the exemplary fill port 112 (FIG. 1) may be about 0.5 inch to about 1 inch, while the thickness (FIG. 5) may be about 0.25 inch to about 1 inch. It should also be noted here that fill ports which are carried by the infusion device housing (described below) may be of any suitable configuration and may include, for example, a housing, a septum and a needle stop.

The fill port 114 is identical to fill port 112 in the exemplary implantable infusion device 100 illustrated in FIGS. 1-4. Differences in the size and/or shape of the fill ports may, however, also be used to distinguish one fill port from the other. To that end, the exemplary infusion device 100a illustrated in FIG. 7 is substantially similar to infusion device 100 and similar elements are represented by similar reference numerals. Here, however, fill port 114a is larger than fill port 112. The size difference between the fill ports 112 and 114a should be substantial, i.e. large enough to be readily identified during a fill or evacuation procedure, and the percentage difference may, for example, range from about 50% to about 100%.

It should also be noted that, as alluded to above, the delivery lumens 136 and 138 in the infusion device 100a are located in separate catheters 200 and 202. The outlet ports may be located on the same side of the header assembly, as they are in the embodiment illustrated in FIG. 1. Here, however, the outlet ports (not shown) are on opposite sides of header assembly 170a. The exemplary infusion device 100a also includes a pair of side ports 168 so that the delivery lumens 136 and 138 within catheters 200 and 202 may be individually accessed. Such a separate catheter and side port configuration may be employed in conjunction with the infusion devices that are described above and below with a single catheter and side port, and a single catheter and side port configuration may be employed in conjunction with those infusion devices described above and below with separate catheters and side ports.

Turning to FIG. 8, examples of differently shaped fill ports 112 and 115 are shown. Such differently shaped ports may be employed, for example, in place of the ports infusion devices 100 and 100a.

The exemplary infusion device 100b illustrated in FIG. 9 is substantially similar to infusion device 100 in some respects, and to infusion device 100a in others, and similar elements are represented by similar reference numerals. Here, however, fill port 114b is carried by the housing 102b in conventional fashion, while the fill port 112 is connected to the remainder of the infusion device 100b by way of the tube 116.

The exemplary implantable infusion devices 100-100b described above, and infusion devices 100c-100k described below, may be included in an infusion device system that also includes a clinician's programming unit. To that end, the exemplary system 10 illustrated in FIG. 10 includes the infusion device 100 and a clinician's programming unit 300. The exemplary clinician's programming unit 300 includes a housing 302, a display 304, a keypad 306, a battery or other power source, a controller, such as a microprocessor, microcontroller or other control circuitry, memory, and a communication device (including an antenna if necessary). Although the present inventions are not limited to any particular communication device, the exemplary communication device is a telemetry device that transmits an RF signal at a specified frequency. The RF signal may, in some instances, be a carrier signal that carries bit streams. The communication device is configured to send signals to and receive signals from the communication device 156 in the implantable infusion device 100 by way of the antenna. Other exemplary communication devices include oscillating magnetic field communication devices, static magnetic field communication devices, optical communication devices, ultrasound communication devices and direct electrical communication devices. In some instances, the remote control may also include an audible alarm.

The exemplary clinician's programming unit 300 may be used to perform a variety of conventional control functions including, but not limited to, turning the infusion device 100 ON or OFF and programming various infusion device parameters. Examples of such parameters include, but are not limited to, delivery profile parameters such as the rate of delivery of a given medication, the time at which delivery of a medication is to commence, and the time at which delivery of a medication is to end. Additionally, the implantable infusion device 100 may transmit signals to the clinician's programming unit 300 to provide status information about the infusion device 100 that may be stored in memory and/or displayed on the display 304. Examples of such status information include, but are not limited to, the state of charge of the battery, the amount of medication remaining in the reservoirs, the amount of medication that has been delivered during a specified time period, and the presence of a catheter blockage. The signals from the infusion device 100 may also be indicative of sensed physiological parameters in those instances where the infusion device is provided with physiological sensors (not shown). Additionally, and as described in greater detail below with reference to FIGS. 13-16 and 19-21, the clinician's programming unit 300 may be used to control various aspects of the operation of implantable infusions devices during fill or evacuation procedures.

Figure 12:
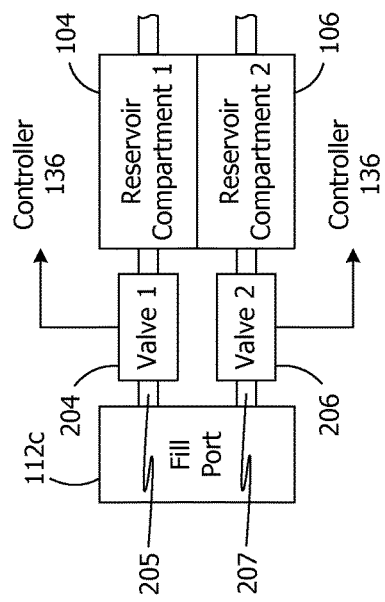
FIG. 12 is a block diagram of a portion of the implantable infusion device illustrated in FIG. 11.
Figure 11:
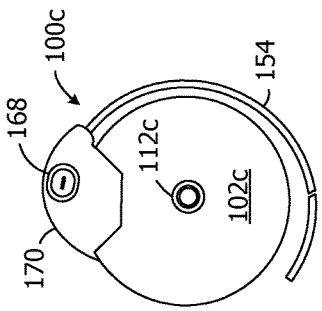
FIG. 11 is a plan view of an implantable infusion device in accordance with one embodiment of a present invention.

Infusion devices in accordance with at least some of the present inventions may also be configured to facilitate fill and evacuation procedures for more than one reservoir compartment by way of a single fill port. As used herein, the phrase "a single fill port" is a limiting phrase which indicates that there is only one fill port on the infusion device. One example of such an infusion device is generally represented by reference numeral 100c in FIG. 11. The exemplary infusion device 100c is substantially similar to infusion device 100 and similar elements are represented by similar reference numerals. Here, however, the infusion device 100c includes a single fill port 112c that is carried by the housing 102c. The single fill port 112c is connected to the first and second reservoir compartments 104 and 106 (FIG. 12) by way of a pair of controllable valves 204 and 206 that control flow through a pair of flow paths 205 and 207 which extend from the single fill port to the reservoir compartments. The valves 204 and 206 open and close in response to instructions from the controller 136. Suitable valves include, but are not limited to, solenoid valves, butterfly valves and needle valves. In those instances where the first reservoir compartment 104 is to receive fluid by way of the fill port 112c, the first valve 204 will be open and the second valve 206 will be closed. Similarly, in those instances where the second reservoir compartment 106 is to receive fluid by way of the fill port 112c, the first valve 204 will be closed and the second valve 206 will be open. The fill port 112c and valves 204 and 206 may also be used to withdraw fluid from the reservoir compartments 104 and 106. The default state of the first and second valves 204 and 206 is the closed state and, if they are opened, the controller 136 may be configured to close an opened valve after a predetermined period, such as a short time after the estimated time to complete the refill (e.g. 3 minutes when the estimated refill time is 2 minutes). The controller 136 may also be configured to allow the automatic closure function to be overridden so that the valve will stay open substantially longer than the estimated time to complete the refill (e.g. stay open for 10 minutes or an hour when the estimate is 2 minutes) before automatically closing, or to stay open until instructed to close.

One exemplary fill procedure involving the infusion device 100c involves using the clinician's programming unit 300 (or other suitable device) to instruct the infusion device controller 136 to open the desired valve when appropriate. The clinician's programming unit 300 may use the display 304 to display various screens that guide the clinician through a fill or evacuation process. One exemplary series of screens is illustrated in FIGS. 13-16. Referring first to FIG. 13, the first screen allows the clinician to indicate that the fill needle has been inserted into the port 112e. The second screen (FIG. 14) allows the clinician to select the reservoir to be filled or evacuated. The clinician's programming unit 300 may also display the infusible substance stored in each reservoir, based on the stored records for the patient, in order to reduce the likelihood of error. The clinician's programming unit 300 will instruct infusion device controller 136 to open the associated valve, i.e. the second valve 204 in illustrated example. The next screen (FIG. 15) indicates how long the valve will remain open and, should the clinician complete the fill or evacuation procedure prior to the end of the predetermined period, allow the clinician to close the opened valve prior to the end of the predetermined period. If, on the other hand, the valve closes prior to the end of the fill or evacuation procedure, the clinician will be given the opportunity to reopen the valve (FIG. 16).

Another exemplary infusion device is generally represented by reference numeral 100d in FIG. 17. Infusion device 100d is substantially similar to infusion device 100 and similar elements are represented by similar reference numerals. Here, however, the infusion device 100d includes first and second fill ports 112d and 114d that are carried by the housing 102d and respectively connected to the first and second reservoir compartments 104 and 106. The exemplary infusion device 100d also includes a pair of needle detectors 208 and 210 that are respectively associated with fill ports 112d and 114d and are connected to the controller 136. Although the present inventions are not limited to any particular type of needle detector, suitable needle detectors are disclosed in U.S. Pat. Nos. 4,573,994 and 6,962,580, which are incorporated herein by reference. Needle detectors may be configured to detect the needle through the use of, for example, a mechanical switch, a magnetic switch, a Hall effect sensor, an electric field, a conductive needle, a magnetic field, and/or an inductor. The information provided by the needle detectors 208 and 210 allows the clinician to confirm that a needle has, in fact, been received within the intended port.

The needle detectors 208 and 210 consume power when in use and, accordingly, the controller 136 may be configured to maintain the needle detectors in a deactivated state unless a fill or evacuation procedure is being performed. The clinician's programming unit 300 (or other suitable device) may be used to instruct the infusion device controller 136 to activate the needle detectors 208 and 210. The clinician's programming unit 300 (or other suitable device) may also be used to instruct the infusion device controller 136 to deactivate the needle detectors 208 and 210. Alternatively, or in addition, the controller 136 may be configured to automatically deactivate the needle detectors 208 and 210 at the end of a predetermined period (e.g. 4-5 minutes). The clinician's programming unit 300 (or other suitable device) may also be configured to extend this time period to, for example, provide additional time to attend to issues that may arise with a needle or the patient.

The information concerning the needle detectors 208 and 210 may be conveyed to the clinician in a variety of ways. For example, the display 304 on the clinician's programming unit 300 may be used to activate the needle detectors 208 and 210 (FIG. 19) and a visible and/or audible indication that the needle detectors are activated may also be provided (FIG. 20). The amount of activation time remaining may also be displayed. When a needle is inserted into one of the first and second fill ports 112d or 114d and is sensed by the associated needle detector 208 or 210, the detection information will be transmitted to the clinician's programming unit 300. The fill ports 112d or 114d in which the needle has been detected may then be identified on the display 304, as is illustrated for example in FIG. 21. The infusible substance stored in the associated reservoir compartment 104 or 106 may also be displayed, based on the stored records for the patient, in order to reduce the likelihood of error. Additionally, the clinician will be given the opportunity to withdraw the needle and reactivate the detectors 208 and 210, which is useful in those instances where the needle was inserted into the wrong fill port. The above-described information may also be provided to the clinician by the clinician's programming unit 300 in audible form.

It should also be noted here that, in other implementations, the infusion device 100d may be configured to provide audible information concerning needle detection. For example, the controller 136 may be configured to actuate audible alarm 166 (FIG. 2) when a needle is sensed in one of the fill ports 112d and 114d. One sound could represent the first fill port 112d, and two sounds could represent the second fill port 114d in some implementations. Audible information concerning the drug associated with the sensed port and/or refill information concerning the drug associated with the sensed port (e.g. drug name and/or "last filled on" date) may also be provided.

Another exemplary infusion device is generally represented by reference numeral 100e in FIG. 22. Infusion device 100e is substantially similar to infusion devices 100 and 100d and similar elements are represented by similar reference numerals. Here, however, the first and second fill ports 112e and 114e are located in spaced relation to the housing 102e, but are adjacent to one another and share a common housing 172e. First and second needle detectors 208 and 210 are carried within the housing 172e and are respectively associated with first and second fill ports 112e and 114e. The first and second fill ports 112e and 114e may be connected to the first and second reservoir compartments 104 and 106 by a single multi-lumen tube 116e (as shown) or by individual tubes. As illustrated in FIG. 24, the multi-lumen tube 116e includes first and second fluid lumens 212 and 214, as well as a lumen 216 for wires (not shown) that connect the needle detectors 208 and 210 to the controller 136. With respect to fill and evacuation procedures, information from the needle detectors 208 and 210 in the exemplary infusion device 100e may be conveyed and used in the manner described above with reference to the infusion device 100e and FIGS. 19-21.

The shape of the implantable infusion device housing may also be used to provide the clinician with information concerning the identity of the fill ports through a tactile examination (or "palpation") of the patient and device. For example, a housing may be provided with at least one palpable landmark that is associated with a single one of the fill ports, such as the first fill port in a two fill port device. Alternatively, each fill port may be associated with its own palpable housing landmark and the landmarks may be palpably distinguishable from one another.

One example of an infusion device with a palpable housing is generally represented by reference numeral 100f in FIG. 25. Infusion device 100f is substantially similar to infusion device 100d and similar elements are represented by similar reference numerals. For example, the infusion device 100f includes first and second fill ports 112f and 114f that are carried by a housing 102f and are respectively connected to the first and second reservoir compartments 104 and 106. The exemplary infusion device 100f also includes a pair of needle detectors 208 and 210 (FIG. 18) that are respectively associated with fill ports 112f and 114f and are connected to the controller 136. To further assist the clinician, the housing 102f is configured to facilitate identification of the first and second fill ports 112f and 114f by palpation of the abdomen, or other region in which the infusion device is located, and the housing. Put another way, some aspect of the housing 102f, other than the ports themselves, will allow the clinician to identify and distinguish between the fill ports 112f and 114f by feeling the housing.

In the illustrated implementation, the housing 102f has an offset shape and defines a pair of indentations 218 and 220 in the housing perimeter 222 that extends around the first and second fill ports 112f and 114f. The indentations 218 and 220, which act as palpable landmarks, face in different directions and, in the exemplary embodiment, face in opposite directions. More specifically, in orientation illustrated in FIG. 25, indentation 218 faces upwardly while indentation 220 faces downwardly. In those instances where the exemplary infusion device 100f is implanted in the orientation illustrated in FIG. 25, the clinician will know that the first fill port 112f is adjacent to the upwardly facing indentation 218 and that the second fill port 114f is adjacent to the downwardly facing indentation 220.

In addition, and regardless of orientation, the clinician will know that the first fill port 112f generally faces the header 170 and that the second fill port 114f generally faces away from the header. The housing perimeter 222 may also be used to identify the fill ports. For example, moving along the perimeter 220 from header 170, the perimeter bends outwardly adjacent to the first fill port 112f and bends inwardly adjacent to the second fill port 114f. As such, even in those instances where the infusion device rotates over time after implantation into the patient, the clinician will be able to identify the indentations by locating the header assembly 170 in addition to the indentations 218 and 220.

Figure 28:
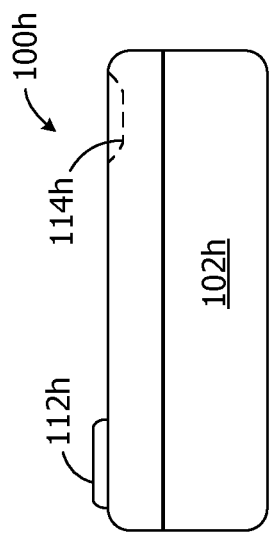
FIG. 28 is an end view of the implantable infusion device illustrated in FIG. 27.
Figure 27:
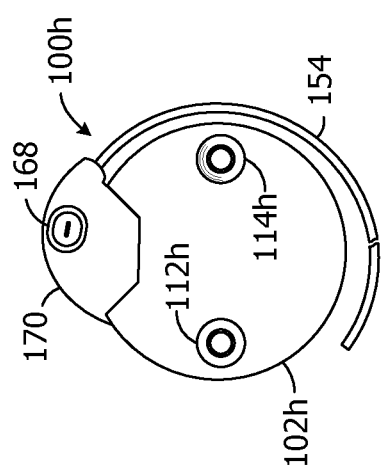
FIG. 27 is a plan view of an implantable infusion device in accordance with one embodiment of a present invention.

Housings that facilitate individual identification of the first and second fill ports by palpation are not limited to the exemplary embodiment illustrated in FIG. 25. By way of example, but not limitation, the exemplary infusion device 100g illustrated in FIG. 26, which is otherwise identical to infusion device 100f, includes a housing 102g with an indentation 218 or other discontinuity adjacent to fill port 112g and no indentation or other discontinuity adjacent to fill port 114g. During a tactile examination of the patient, fill port 112g will be identified by the presence of the indentation and fill port 114g will be identified by the absence of the indentation. The exemplary infusion device 100h illustrated in FIGS. 27 and 28, which is otherwise identical to infusion device 100d, includes a housing 102h and first and second fill ports 112h and 114h. A portion of the first fill port 112h protrudes outwardly from (and relative to) the outer surface of the housing 102h, while the second fill port 114h is recessed into the housing such that no portion of the second fill port protrudes outwardly relative to the remainder of the outer surface of the housing. During a tactile examination of the patient, fill ports 112h and 114h will be differentiated from one another by the respective protruding and recessed characteristics thereof.

After the clinician has identified the desired fill port on the infusion device 100f or 100g or 100h by palpation (or "tactile examination") of the housing 102f or 102g or fill ports 112h/114h, a fill or evacuation procedure may be performed in, for example, the manner described above in the context of infusion device 100d and the clinician's programming unit 300. The functionality associated with the needle detectors 208 and 210 allows the clinician to confirm that the correct fill port was accessed. It should be noted, however, that the needle detectors 208 and 210 may be omitted in other implementations. Here, the clinician will rely solely on palpation to identify and distinguish between fill ports 112f/114f and fill ports 112g/114g and fill ports 112h/114h during a fill or evacuation procedure.

As alluded to above, another issue associated with implantable infusion devices and the clinician's ability to locate a fill port is rotation of the device after implantation into the patient. One example of an implantable infusion device that is configured to reduce the likelihood of post-implantation rotation is generally represented by reference numeral 100i in FIGS. 29-32. Infusion device 100i is substantially similar to infusion device 100d and similar elements are represented by similar reference numerals. For example, the infusion device 100i includes first and second fill ports 112i and 114i that are carried by a housing 102f and are respectively connected to the first and second reservoir compartments 104 and 106. The exemplary infusion device 100i also includes a pair of needle detectors 208 and 210 (FIG. 18) that are respectively associated with fill ports 112i and 114i and are connected to the controller 136. Here, however, the exemplary housing 102i does not have a generally flat disk shape, as does housing 102i and, instead, is shaped in a manner that corresponds to the curvature of the associated portion of the patient's body.

The exemplary housing 102i is a three-dimensional object that defines two relatively large (or "major") dimensions $MD_1$ and $MD_2$ and a thickness T, which is substantially less than the major dimensions. In the orientation illustrated in FIG. 29, $MD_1$ is the height and $MD_2$ is the width. The exemplary housing 102i also has convex front wall 224 and a concave rear wall 226, and the thickness dimension is the distance between the front and rear walls. The fill ports 112i and 114i are associated with the convex front wall 224 in the illustrated embodiment.

Figure 32:
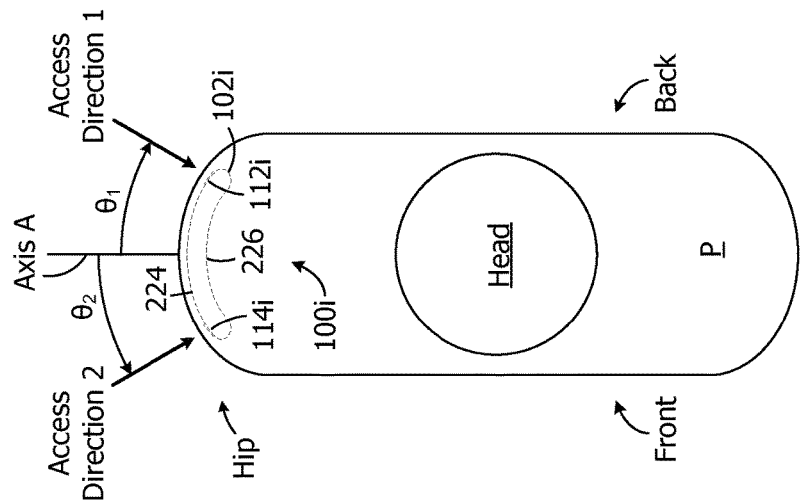
FIGS. 31 and 32 are diagrammatic views showing the implantable infusion device illustrated in FIG. 29 implanted in a person.
Figure 31:
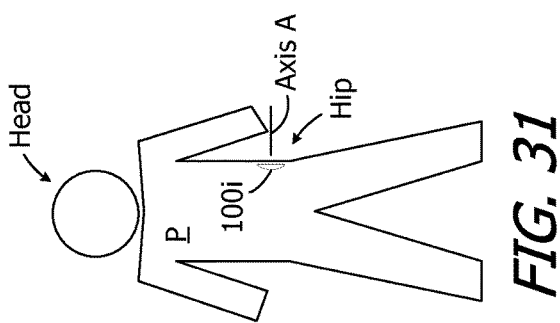
Figure 29:
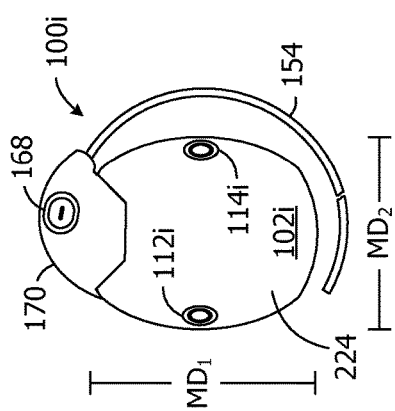
FIG. 29 is a plan view of an implantable infusion device in accordance with one embodiment of a present invention.
Figure 30:
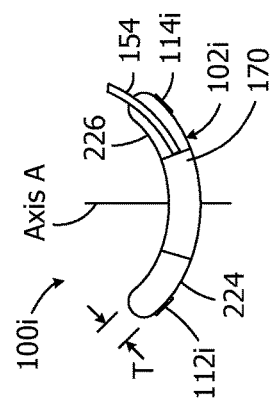
FIG. 30 is an end view of the implantable infusion device illustrated in FIG. 29.

Referring to FIGS. 30-32, the exemplary infusion device 100i may be implanted, for example, adjacent to the patient P's hip. Tissue will press against the convex front wall 224 and concave rear wall 226 of the implanted housing 102i, thereby possibly reducing the likelihood that the infusion device 100i will rotate about an axis that passes through the front and rear walls (e.g. axis A) should the sutures that hold the device in place break, as compared to an infusion device which has generally flat front and rear walls.

The curved configuration of the housing 102i, and the fact that the first and second fill ports 112i and 114i are located on opposite sides of the apex of the convex front wall 224, also results in different needle access angles for the first and second fill ports, which facilitates port differentiation. More specifically, and referring to FIG. 32, the first and second needle access directions for the first and second fill ports 112i and 114i are generally perpendicular to the fill ports and, given the curvature of the housing 102i, define needle access angles $\theta_1$ and $\theta_2$ that extend in different directions from axis A. In the illustrated implementation, needle access angle $\theta_1$ extends toward the patient's back and needle access angle $\theta_2$ extends toward the patient's front. Put another way, the first needle access direction is pivoted towards the patient's back and the second needle access direction is pivoted towards the patient's front.

After the clinician has identified the desired fill port on the infusion device 100i by virtue of its expected location relative to an anatomical reference point (e.g. laterally to the right or laterally to the left of the hip) and/or the access angle of the needle, a fill or evacuation procedure may be performed in, for example, the manner described above in the context of infusion device 100d and the clinician's programming unit 300. The functionality associated with the needle detectors 208 and 210 allows the clinician to confirm that the correct fill port was accessed. It should be noted, however, that the needle detectors 208 and 210 may be omitted in other implementations. Here, the clinician will rely solely on anatomical landmarks, and the infusion device's relationship thereto and/or the access angle of the needle, to distinguish between the fill ports 112i and 114i during a fill or evacuation procedure.

It should be noted here that the housings that are shaped or otherwise configured to prevent rotation are not limited to infusion devices with multiple reservoirs and multiple fill ports and may also be incorporated into infusion devices that have a single reservoir and a single fill port. Other reasons to prevent rotation of implantable infusion devices include, for example, simply making it easier for the clinician to insert a needle into the fill port because the fill port will remain in the expected location. Post-implantation rotation can also put strain on catheter, can pull the end of the catheter from its proper position (e.g. within spine), can cause catheter fatigue at the connection to the pump, which leads to breaks and leaks, can cause disconnections at the pump or at the spinal connection of a two-part catheter, and can cause tissue irritation or erosion in the pump pocket.

Figure 34:
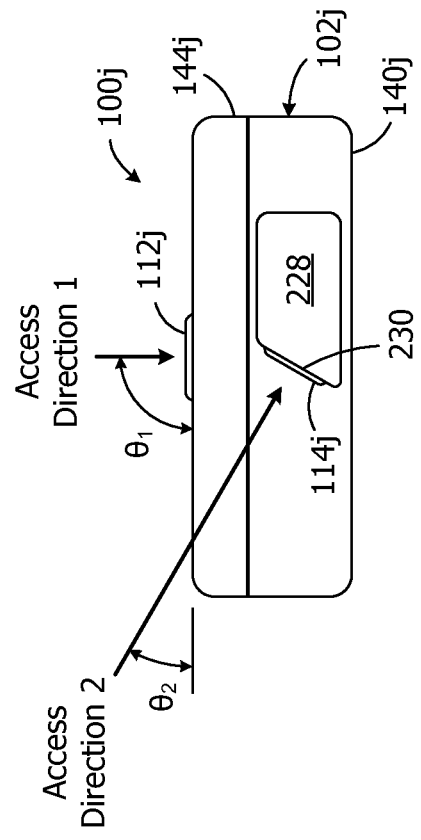
FIG. 34 is an end view of the implantable infusion device illustrated in FIG. 33.
Figure 33:
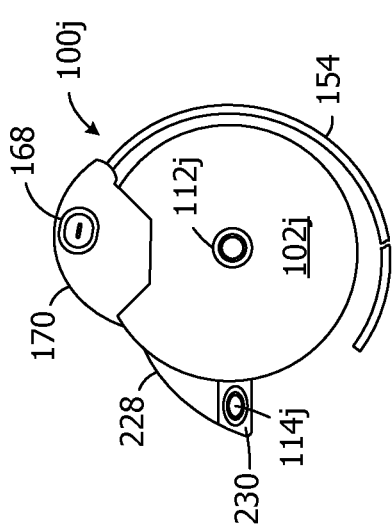
FIG. 33 is a plan view of an implantable infusion device in accordance with one embodiment of a present invention.

Turning to FIGS. 33 and 34, another example of an implantable infusion device that facilitates access port identification though palpation and/or needle access angle is generally represented by reference numeral 100j. Infusion device 100j is substantially similar to infusion device 100d and similar elements are represented by similar reference numerals. For example, the infusion device 100j includes first and second fill ports 112j and 114j that are associated with a housing 102j and are respectively connected to the first and second reservoir compartments 104 and 106. The exemplary infusion device 100j also includes a pair of needle detectors 208 and 210 (FIG. 18) that are respectively associated with fill ports 112j and 114j and are connected to the controller 136.

With respect to the identification of the first and second fill ports 112j and 114j by palpation, the infusion device 100j includes a port support 228 located on, and extending radially outwardly from, the outer perimeter of the housing 102j. One of the ports (e.g. port 112j) is located at the center of the housing and the other port (e.g. port 114j) carried by the port support 228. The port support 228 may be an integral part of the housing bottom portion 140j (as shown), an integral part of the cover 144j, secured to the bottom portion or cover, or may be a two-part device having portions that are integral with or are secured to both the bottom portion and the cover. A flow path from the second port 114j to the associated reservoir may be formed in any suitable manner.

The orientation of the first and second fill ports 112j and 114j also results in different needle access angles. In particular, the access direction of the first fill port 112j is essentially perpendicular to the surface of the cover 144j that is associated with the first fill port and, accordingly, the first access angle $\theta_1$ is about 90 degrees, measured from a horizontal plane defined by (or associated with) the cover surface. The port support 228 has an angled surface 230 for the second port 114j that results in a different access direction and access angle for the second port. For example, the second access angle $\theta_2$ may be about 10-30 degrees, measured from the horizontal plane.

After the clinician has identified the desired fill port on the infusion device 100j by palpation (or "tactile examination") of the housing 102j and port support 228 and/or the needle access angle, a fill or evacuation procedure may be performed in, for example, the manner described above in the context of infusion device 100d and the clinician's programming unit 300. The functionality associated with the needle detectors 208 and 210 allows the clinician to confirm that the correct fill port was accessed. It should be noted, however, that the needle detectors 208 and 210 may be omitted in other implementations. Here, the clinician will rely solely on palpation and needle access angle to identify and distinguish between fill ports 112j/114jf during a fill or evacuation procedure.

Another infusion device that is configured to facilitate fill and evacuation procedures for more than one reservoir compartment by way of a single fill port is generally represented by reference numeral 100k in FIG. 35. The exemplary infusion device 100k is substantially similar to infusion device 100c and similar elements are represented by similar reference numerals. For example, the infusion device 100k includes a single fill port 112k that is carried by the housing 102k and is connected to the first and second reservoir compartments 104 and 106. Here, however, the single fill port 112k is configured to accommodate needles with different outlet aperture locations. A needle having an outlet aperture in a first location will be in fluid communication with the first reservoir compartment 104 (FIG. 2) when the needle is fully inserted into the fill port 112k, and a needle having an outlet aperture in a second location will be in fluid communication with the second reservoir compartment 106 when the needle is fully inserted into the fill port. As used herein, a needle is "fully inserted" when it is inserted into the fill port to such an extent that further movement in the insertion direction is prevented. Accordingly, the clinician simply employs a needle which corresponds to the intended reservoir compartment during fill and evacuation procedures, as is described below with reference to FIGS. 37 and 38. The controllable valves 204 and 206 associated with infusion device 100c (FIG. 12) need not be present unless desired for additional safety.

Turning to FIG. 36, the exemplary fill port 112k includes a housing 232, first and second spacers 234 and 236, first and second septums 238 and 240, and a housing end wall 242. The fill port 112k also has first and second longitudinally spaced (i.e. spaced in the needle access direction) fluid receiving regions 244 and 246 that are isolated from one another such that fluid flow therebetween is prevented. The first fluid receiving region 244 is located between the first and second septums 238 and 240, and the second fluid receiving region 246 is located between the second septum 240 and the housing end wall 242. The housing 232 includes a lumen 248 through which a needle may be inserted. The first and second spacers 234 and 236, which are annular structures, include respective apertures 250 and 252 that are aligned with housing apertures 254 and 256. As such, fluid flow between the first fluid receiving region 244 and the first reservoir compartment occurs by way of apertures 250 and 254, while fluid flow between the second fluid receiving region 246 and the second reservoir compartment occurs by way of apertures 252 and 256. The septums 238 and 240 may, for example, be self-healing septums formed from materials such as silicone. Septum 240 prevents fluid flow between the fluid receiving regions 244 and 246. In some instances, such as the illustrated implementation, annular filters 258 and 260 (e.g. sintered metallic filters) may also be provided.

A needle that is configured to make a fluidic connection with the first fluid receiving region 244 of the fill port 112k and, accordingly, the first reservoir compartment 104, is generally represented by reference numeral 310 in FIG. 37. The needle 310 may be a non-coring needle which reduces the likelihood that it will damage the septums 238 and 240. To that end, the exemplary needle 310 includes an elongated tubular body 312, with an internal lumen, and a sharpened end portion 314. One or more outlet apertures 316 pass through the tubular body 312 to the internal lumen. The configuration of the fill port 112k, and the distance between the distal tip of the sharpened end portion 314 and the aperture 316, are such that the outlet aperture 316 is located within the first fluid receiving region 244 when the needle 310 is fully inserted into the fill port, i.e. when the distal tip of the sharpened end portion 314 is in contact with the housing end wall 242.

A needle that is configured to make a fluidic connection with the second fluid receiving region 246 of the fill port 112k and, accordingly, the second reservoir compartment 106 is generally represented by reference numeral 310a in FIG. 38. The needle 310a is substantially similar to needle 310 and similar elements are represented by similar reference numerals. Here, however, the distance between the distal tip of the sharpened end portion 314 and the outlet aperture 316 is such that the aperture 316 is located within the second fluid receiving region 246 when the needle 310a is fully inserted into the fill port, i.e. when the distal tip of the sharpened end portion 314 is in contact with the housing end wall 242.

The fill port 112k is, as noted above, carried by the infusion device housing 102k in the illustrated embodiment. In other implementations, a similar fill port that is configured to accommodate two different needles in the manner described above may be located in spaced relation to the housing in a manner similar to the fill ports illustrated in FIG. 22.

Although the inventions disclosed herein have been described in terms of the preferred embodiments above, numerous modifications and/or additions to the above-described preferred embodiments would be readily apparent to one skilled in the art. By way of example, but not limitation, a single fluid transfer device may be used in combination with multiple reservoir compartments. It is intended that the scope of the present inventions extend to all such modifications and/or additions and that the scope of the present inventions is limited solely by the claims set forth below.

We claim:
1. An implantable infusion device, comprising:
   an infusion device housing;
   first and second reservoir compartments associated with the infusion device housing;
   at least one fluid transfer device operably connected to the first and second reservoir compartments; and
   a fill port including
      a fill port housing with first and second outlet apertures and an end wall,
      first and second longitudinally spaced septums within the fill port housing such that the second outlet aperture is located between the second septum and the end wall,
      a first fluid receiving region within the fill port housing between the first and second septums and a second fluid receiving region within the fill port housing between the second septum and the end wall, the first and second fluid receiving regions being isolated from one another by the second septum such that fluid flow therebetween is prevented, the first fluid receiving region being operably connected to the first reservoir compartment by the first outlet aperture and a first flow path and the second fluid receiving region being operably connected to the second reservoir compartment by the second outlet aperture and a second flow path, a first annular filter having an inner perimeter defining the first fluid receiving region and an outer perimeter facing the first outlet aperture and in contact with a first cylindrical surface within the fill port housing, and a second annular filter having an inner perimeter defining the second fluid receiving region and an outer perimeter facing the second outlet aperture and in contact with a second cylindrical surface within the fill port housing;

the respective configurations of the first annular filter and the fill port housing being such that the fluid passes through the inner and outer perimeters of the first annular filter as the fluid flows from the first fluid receiving region to the first outlet aperture; and the respective configurations of the second annular filter and the fill port housing are such that the fluid passes through the inner and outer perimeters of the second annular filter as the fluid flows from the second fluid receiving region to the second outlet aperture.

2. An implantable infusion device as claimed in claim 1, wherein the at least one fluid transfer device comprises a first fluid transfer device operably connected to the first reservoir compartment and a second fluid transfer device operably connected to the second reservoir compartment.

3. An implantable infusion device as claimed in claim 2, further comprising:
a first delivery lumen operably connected to the first fluid transfer device; and
a second delivery lumen operably connected to the second fluid transfer device.

4. An implantable infusion device as claimed in claim 3, wherein the first and second delivery lumens are located within different catheters.

5. An implantable infusion device as claimed in claim 1, further comprising:
a reservoir and a pressure transmissive partition located within the reservoir, the first and second reservoir compartments being located within the reservoir on opposite sides of the pressure transmissive partition.

6. An implantable infusion device as claimed in claim 1, wherein the fill port is carried by the infusion device housing.

7. An implantable infusion device system, comprising:
an implantable infusion device including
an infusion device housing,
first and second reservoir compartments associated with the infusion device housing,
at least one fluid transfer device operably connected to the first and second reservoir compartments, and
a fill port including
a fill port housing with first and second outlet apertures and an end wall,
first and second longitudinally spaced septums within the fill port housing such that the second outlet aperture is located between the second septum and the end wall,
a first fluid receiving region within the fill port housing between the first and second septums and a second fluid receiving region within the fill port housing between the second septum and the end wall, the first and second fluid receiving regions being isolated from one another by the second septum such that fluid flow therebetween is prevented, the first fluid receiving region being operably connected to the first reservoir compartment by the first outlet aperture and a first flow path and the second fluid receiving region being operably connected to the second reservoir compartment by the second outlet aperture and a second flow path, a first annular filter having an inner perimeter defining the first fluid receiving region and an outer perimeter facing the first outlet aperture and in contact with a first cylindrical surface within the fill port housing, and a second annular filter having an inner perimeter defining the second fluid receiving region and an outer perimeter facing the second outlet aperture and in contact with a second cylindrical surface within the fill port housing, the respective configurations of the first annular filter and the fill port housing being such that the fluid passes through the inner and outer perimeters of the first annular filter as the fluid flows from the first fluid receiving region to the first outlet aperture, and the respective configurations of the second annular filter and the fill port housing are such that the fluid passes through the inner and outer perimeters of the second annular filter as the fluid flows from the second fluid receiving region to the second outlet aperture;

a first needle, including a sharpened distal end portion and an outlet aperture, configured such that the outlet aperture of the first needle is located within the first fluid receiving region when the first needle is fully inserted into the fill port; and a second needle, including a sharpened distal end portion and an outlet aperture, configured such that the outlet aperture of the second needle is located within the second fluid receiving region when the second needle is fully inserted into the fill port.

8. An implantable infusion device system as claimed in claim 7, wherein the at least one fluid transfer device comprises a first fluid transfer device operably connected to the first reservoir compartment and a second fluid transfer device operably connected to the second reservoir compartment.

9. An implantable infusion device system as claimed in claim 8, further comprising:
a first delivery lumen operably connected to the first fluid transfer device; and
a second delivery lumen operably connected to the second fluid transfer device.

10. An implantable infusion device system as claimed in claim 9, wherein the first and second delivery lumens are located within different catheters.

11. An implantable infusion device system as claimed in claim 7, further comprising:
a reservoir and a pressure transmissive partition located within the reservoir, the first and second reservoir compartments being located within the reservoir on opposite sides of the pressure transmissive partition.

12. An implantable infusion device system as claimed in claim 7, wherein the fill port is carried by the infusion device housing.

* * * * *